United States Patent [19]

Honda et al.

[11] Patent Number: 4,474,969
[45] Date of Patent: Oct. 2, 1984

[54] PREPARATION PROCESS OF INDOLE

[75] Inventors: Tadatoshi Honda, Hiratsuka; Kazuhiro Terada, Yokohama, both of Japan

[73] Assignee: Mitsui Toatsu Chemicals, Incorporated, Tokyo, Japan

[21] Appl. No.: 502,016
[22] PCT Filed: Aug. 25, 1982
[86] PCT No.: PCT/JP82/00337
    § 371 Date: Apr. 22, 1983
    § 102(e) Date: Apr. 22, 1983
[87] PCT Pub. No.: WO83/00691
    PCT Pub. Date: Mar. 3, 1983

[30] Foreign Application Priority Data

Aug. 25, 1981 [JP] Japan ................................. 56-132096

[51] Int. Cl.$^3$ ............................................ C07P 209/08
[52] U.S. Cl. .................................................. 548/508
[58] Field of Search ......................... 548/508; 260/699

[56] References Cited
U.S. PATENT DOCUMENTS 2,438,721  3/1948  Sensel et al. ......................... 260/699
2,618,660  11/1952  Payne et al. ......................... 260/699
3,656,911  4/1972  Hobbs ................................. 260/699

FOREIGN PATENT DOCUMENTS 110672   9/1981  Japan ................................. 548/508
150062  11/1981  Japan ................................. 548/508
169668  12/1981  Japan ................................. 548/508

Primary Examiner—Richard Raymond
Assistant Examiner—D. B. Springer
Attorney, Agent, or Firm—Fisher, Christen & Sabol

[57] ABSTRACT

Preparation process of indole from aniline and ethylene glycol. Upon preparing indole by reacting aniline and ethylene glycol in a gas phase and in the presence of a catalyst, ethylene glycol is charged in portions to a multiplicity of catalyst stages formed by dividing a catalyst bed and connected in series. This divided supply of ethylene glycol permits the suppresing of the decomposition of ethylene glycol, even if the molar ratio of feed aniline to total feed ethylene glycol is small. The above process permits making the yield of indole large and reducing the amount of unreacted aniline to be separated and recovered from the reaction effluent.

6 Claims, 1 Drawing Figure

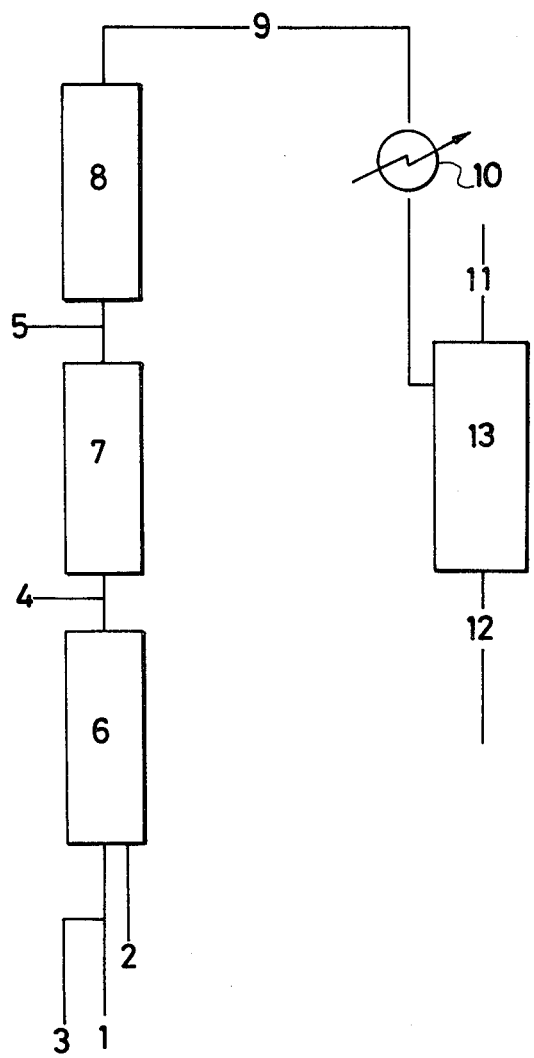

PREPARATION PROCESS OF INDOLE

DESCRIPTION

1. Technical Field

This invention relates to a process for preparing indole from aniline and ethylene glycol.

2. Background Art

This invention relates to an improved preparation process of indole using aniline and ethylene glycol as raw materials.

More specifically, this invention relates, upon preparing indole from aniline and ethylene glycol in the presence of a catalyst, to a feeding method of ethylene glycol which is one of the starting materials.

Indole is known as a raw material for the chemical industry. Notably in recent years, it has become an important material as a raw material for the syntheses of various fragrant compounds and amino acids.

Several attempts have heretofore been made to synthetically obtain indole. Many of such attempts resulted in the occurrence of lots and/or many by-products and required costly starting materials. In addition, they involved many steps to reach indole, and were irksome to practice. However, a preparation process of indole from aniline and ethylene glycol has recently been developed as a one-step preparation process of indole using inexpensive starting materials.

As reaction catalysts for the synthesis of indole from aniline and ethylene glycol, a variety of solid acid catalysts and metallic catalysts have been proposed.

To the knowledge of the present inventors, it seems to be essential, in order to obtain indole with a good yield, to feed a very excess amount of aniline relative to ethylene glycol to the catalyst bed when indole is prepared from aniline and ethylene glycol using various catalysts proposed so far. When preparing indole in the above manner, it is necessary to separate and recover a large amount of aniline contained in the resulting reaction mixture, leading to a problem that the above preparation process requires a very large separation/recovery unit and lots of energy.

The present inventors have carried out an extensive research on the relationship between the molar ratio of aniline to ethylene glycol, both charged into a reactor, and the yield of indole. As a result, it has been found, as described later in a referential example, that the yield of indole on the basis of ethylene glycol increases as the molar ratio of aniline to ethylene glycol becomes greater. Analyses of liquid reaction products and gaseous reaction products have also uncovered that aniline and ethylene glycol are converted into indole in accordance with the following chemical equation (1) but a reaction represented by the following chemical equation (2) also takes place, thereby causing ethylene glycol to undergo a decomposition reaction.

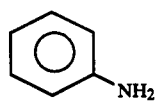  (1)

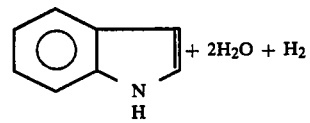

$$HOCH_2CH_2OH \longrightarrow 2CO + 3H_2 \quad (2)$$

The reaction (2) takes place more violently as the molar ratio of aniline to ethylene glycol decreases, thereby leading to a poor yield of indole.

When the molar ratio of aniline to ethylene glycol is small, the reaction (2) is promoted whereas the reaction (1) is suppressed. The following explanation may be given as causes for the above tendency. First of all, the reaction (1) pertaining both aniline and ethylene glycol and the reaction (2) pertaining ethylene glycol only are governed by the partial pressure of each of the reactants. When the molar ratio of aniline to ethylene glycol is small, the partial pressure of aniline in the reaction system becomes smaller and, instead, the partial pressure of ethylene glycol increases and the reaction (2) is more encouraged to take place than the reaction (1). Secondly, as a more important cause than the aforementioned first cause, the reaction (1) is an exothermic reaction of 40-50 Kcal under reaction conditions, while the reaction (2) is an endothermic reaction of 40-50 Kcal. Thus, when the molar ratio of aniline to ethylene glycol is small, heat is produced in accordance with the reaction (1) at an inlet portion of the catalyst bed where the concentration of ethylene glycol is high, leading to the development of a localized high-temperature region (i.e., so-called heat spot). As a result, the reaction (2), which is an endothermic reaction, seems to be promoted at such a heat spot. Therefore, it is gathered that such a heat spot is developed more readily, the decomposition reaction (2) is thus accelerated and the yield of indole is consequently lowered, as the concentration of ethylene glycol increases, in other words, the molar ratio of aniline to ethylene glycol becomes smaller.

The present inventors have carried out an extensive research, on the basis of the above finding, to develop a process which is capable of making the concentration of indole high at the outlet of a reactor without lowering the yield of indole. As a result, it has been found that, when a catalyst bed is divided into a multiplicity of stages, the thus-formed catalyst stages are connected in series and one of the starting materials, ethylene glycol, is fed in portions to all the catalyst stages, the concentration of indole at the outlet of the catalyst bed formed of the catalyst stages connected to one another in series can be increased without lowering the yield of indole, whereby leading to the completion of the process according to this invention.

DISCLOSURE OF THE INVENTION

The present invention provides a process for preparing indole by reacting aniline and ethylene glycol in a gas phase and in the presence of a catalyst, which process comprises feeding ethylene glycol in portions along the flowing direction of the reaction gas passing through a catalyst bed containing the catalyst.

According to the process of this invention, the development of localized heat spots can be suppressed because the concentration of ethylene glycol is rendered uniform throughout the catalyst bed even if the molar ratio of aniline to ethylene glycol, both charged into the reactor, is small. As a result, the decomposition of ethylene glycol, which takes place in accordance with the chemical equation (2), is retarded, resulting in an effect that the yield of indole is not sacrificed. In addition, since the molar ratio of aniline to ethylene glycol, both to be charged into the reactor, can be made smaller, it is possible to increase the concentration of indole at the outlet of the reactor and, at the same time, to decrease the amount of aniline to be separated and recovered from the reaction effluent.

BRIEF DESCRIPTION OF THE DRAWING

The drawing is a schematic illustration of the reaction system employed in Example 1.

BEST MODE FOR CARRYING OUT THE INVENTION

In the preparation process of indole to which the present invention is directed, aniline and ethylene glycol are reacted in the presence of a solid acid catalyst or metallic catalyst.

As solid acid catalysts useful in the practice of the process of this invention, may be mentioned:

(1) catalysts containing the oxide or hydroxide of at least one element selected from Si, Al, B, Sb, Bi, Sn, Pb, Ga, Ti, Zr, Be, Mg, Y, Cu, Ag, Zn, Cd and the Lanthanide elements, such as CdO, $ZnO$—$Sb_2O$—$PbO_2$, $Al_2O_3$—$B_2O_3$, $SiO_2$—CdO, $SiO_2$—$Al_2O_3$, $SiO_2$—MgO, $TiO_2$—$SnO_2$, $TiO_2$—$ZrO_2$, CdO—$Bi_2O_3$, $SiO_2$—$Ce_2O_3$, $SiO_2$—$Y_2O_3$, $SiO_2$—$Bi_2O_3$—BeO, $SiO_2$—$Ga_2O_3$, $SiO_2$—$La_2O_3$, $SiO_2$—ZnO—AgO, $SiO_2$—MgO—CuO, etc. (hereinafter called "catalyst component (1)");

(2) catalysts containing the sulfide or selenide of at least one element selected from Pd, Pt, Cr, Fe, Ni, Co, Zn, Mo, Cd and W, such as PdS, PtS, CrS, FeS, NiS, CoS, ZnS, $MoS_2$, CdS, $WS_2$, ZnSe, CdSe, and the like (hereinafter called "catalyst component (2)");

(3) catalyst containing an inorganic salt, namely, a halide or the carbonate, nitrate, sulfate, phosphate, pyrophosphate, phosphorus molybdate or silicotungstate of at least one element selected from Fe, Tl, Ca, Mn, Bi, Sr, Y, Al, Zn, Cd, Ni, Mg, In, Be, Co, Ga and the Lanthanide elements, such as ferric sulfate, thallium sulfate, calcium sulfate, manganese sulfate, bismuth sulfate, strontium sulfate, yttrium sulfate, cadmium bromide, aluminum sulfate, zinc sulfate, nickel sulfate, cadmium chloride, magnesium sulfate, indium sulfate, beryllium sulfate, cadmium nitrate, cobalt sulfate, zinc aluminum sulfate, magnesium chloride, cadmium sulfate, cadmium phosphate, etc. (hereinafter called "catalyst component (3)").

Furthermore, as exemplary metallic catalysts, may be mentioned catalysts containing at least one element selected from Cu, Ag, Pt, Pd, Ni, Co, Fe, Ir, Os, Ra and Rh (hereinafter called "catalyst component (4)).

Among the above catalysts, the most preferably used catalysts are respectively $SiO_2$—ZnO—AgO for the catalyst group containing the catalyst component (1), cadmium sulfide for the catalyst group containing the catalyst component (2), cadmium sulfate for the catalyst group containing the catalyst component (3), and Ag carried on a carrier having a large specific surface area for the metallic catalysts.

These solid acid catalysts and metallic catalysts may be prepared in accordance with any known method. Namely, the catalyst components (1) among solid acid catalysts may be obtained by either hydrolyzing water-soluble salts of their corresponding catalyst-constituting elements to hydroxides and drying and baking the thus-obtained gels; or subjecting readily-decomposable salts of their corresponding catalyst-constituting elements to thermal decomposition in air.

The catalyst components (2) out of solid acid catalysts may, on the other hand, be prepared by either adding sodium sulfide or potassium selenide to water-soluble salts of their corresponding catalyst-constituting elements; or contacting their corresponding catalyst-constituting elements or their salts to hydrogen sulfide gas or hydrogen selenide gas.

In addition, the catalyst components (4), which are metallic catalysts, may be produced by reducing salts, hydroxides or oxides of their corresponding catalyst-constituting elements with a reducing agent such as hydrogen, formaldehyde, formic acid, phosphorous acid, hydrazine or the like.

These solid acid catalysts and metallic catalysts may be formed of either one of the aforementioned catalyst components (1), (2), (3), and (4), or a mixture of two or more of the catalyst components (1), (2), (3), and (4), which catalyst component or components may optionally be carried on a carrier. As such a carrier, it is possible to use any carrier commonly used in the art. Generally speaking, diatomaceous earth, pumice, titania, silica-alumina, alumina, magnesia, silica gel, activated carbon, activated clay, asbestos and the like may be employed. Catalyst-laden carriers may be prepared by causing these carriers to carry the above-described catalyst components thereon. There is no particular limitation to the amount of a catalyst component to be carried on a carrier. A catalyst component may generally be carried in an amount suitably determined in accordance with the type of a carrier, for example, in an amount of 1–50% based on the carrier.

In the preparation process of indole according to this invention, the reaction between aniline and ethylene glycol is carried out in a gas phase and in the presence of either one of the above-described catalysts. The reactor may be of any one of the fixed bed, fluidized bed and moving bed types. However, a fixed bed-type reactor may usually be used.

Aniline and ethylene glycol are converted into indole by bringing them into contact with a catalyst in vapor forms and under heating conditions. Here, as diluents for aniline and ethylene glycol vapors, a variety of inert gaseous substances may be present together with such vapors. Exemplary inert gaseous substances of the above type may include nitrogen gas, carbon dioxide gas, steam, hydrogen gas, etc. Use of hydrogen gas is particularly preferred, as it is effective to keep the catalyst active. Use of steam may also be preferred to maintain the activity of the catalyst and to increase the yield of indole, because steam serves to suppress the decomposition of ethylene glycol on the catalyst.

Aniline may be charged into a reactor in an amount of 1.0–5.0 moles, and preferably 2.0–3.0 moles per mole of total ethylene glycol also charged into the reactor.

Aniline and ethylene glycol are directly charged into the reactor, either by vaporizing them in advance or in liquid forms, in such a way that the liquid space velocity becomes 0.01–5 liters/liter-catalyst/hour with respect to the catalyst.

The reaction temperature may be in the range of 200°–600° C., and preferably, 250°–500° C.

The reaction may be effected under elevated, normal or reduced pressures.

In the preparation process of indole according to this invention, ethylene glycol is charged into the catalyst bed, in portions, through the inlet of the catalyst bed and several feed ports provided along the flowing direction of the reaction gas.

The essential feature of the process according to the present invention is to make the concentration of ethylene glycol in the catalyst bed uniform therethrough. More specifically, it is a main feature of this invention to make the minimum value M of the molar ratio m of aniline to ethylene glycol (namely, the mole number of aniline per mole of ethylene glycol) in the catalyst bed preferably at least 5, more preferably at least 7, and most preferably 10 or higher. Since it is also an object of this invention to decrease the amount of aniline to be separated and recovered from the reaction effluent, it is desirous to make the molar ratio A of aniline to total ethylene glycol charged into the reactor (i.e., the mole number of aniline per mole of total ethylene glycol charged in portions) not more than 5, and preferably, not more than 3.

There are no particular limitations vested on the number of divided supply ports and dividing ratio, so long as the divided supply of ethylene glycol meets the aforementioned conditions.

The divided supply of ethylene glycol is effected through the raw material inlet of the catalyst bed of the reaction as well as one or more places (hereinafter called feed ports") provided along the catalyst bed and along the flowing direction of the reaction gas. The divided supply of ethylene glycol may preferably, generally speaking, be carried out by dividing the catalyst bed into two or more sections along its length, providing ethylene glycol feed ports at the gas inlet side of the first catalyst stage and between each two adjacent catalyst stages and then charging ethylene glycol in portions through the feed ports.

In view of convenience in operation, ethylene glycol is divided in equal portions to all feed ports including the ethylene glycol portion to be fed together with aniline to the inlet of the catalyst bed. The number of feed ports n required when supplying ethylene glycol in equal portions to all the feed ports may be calculated by the following equation (3) to satisfy the abovementioned conditions.

$$n \geq (M-1)/(A-1) \qquad (3)$$

For instance, when $M=7$ and $A=3$, $n=3$. If $M=10$ and $A=3$, $n=5$. Accordingly, 3-5 feed ports are generally required including the feed port adapted to supply a part of ethylene glycol together with aniline at the inlet of the catalyst bed. However, it should be noted that the number of feed ports is not necessarily limited to such numbers. It is also feasible to charge a part of aniline in portions together with the thus-divided ethylene glycol.

The invention will hereinafter be described in further detail in the following examples.

EXAMPLE 1

An experiment was carried out using the reaction system illustrated in the drawing, in which tubular reactors 6, 7, 8 having an inner diameter of 25 mm and made of stainless steel were each packed with 160 ml of a catalyst having a grain size of 3-4 mm. The tubular reactors were connected in series and used to effect a reaction. As the catalyst, press-formed granular cadmium sulfide was used. Hydrogen gas was supplied at 2 liters/minute to the tubular reactors through a line 2. The catalyst bed was gradually heated from room temperature to 350° C. and maintained at the latter temperature. Aniline and a 33 wt.% aqueous solution of ethylene glycol were charged, respectively, at 75 g/hr. and 16 g/hr. to the tubular reactor 6 from a feed line 1 via a vaporizer. 30 minutes later, the 33 wt.% aqueous solution of ethylene glycol was charged at 16 g/hr. from a feed line 4 via a vaporizer. One hour later, the 33 wt.% aqueous solution of ethylene glycol was charged at 16 g/hr. from a feed line 5 via a vaporizer. A gaseous reaction mixture was passed through a line 9 to a condenser 10, where it was cooled. The thus-cooled reaction mixture was thereafter fed to a gas/liquid separator tank 13, in which it was separated into a liquid portion and a non-condensable gas portion. The non-condensable gas portion was discharged into the atmospheric air through a line 11, whereas the condensate was taken out from time to time through a line 12 for its analysis. An analysis of a condensate obtained during the period of the 24th-27th hours after the initiation of the reaction in which period the activity of the catalyst had been stabilized indicated that the concentration of indole in the condensate was 16.8 wt.%, in other words, the yield of indole was 68% based on ethylene glycol.

EXAMPLES 2, 3 AND 4

Experiments were carried out in the same manner as in Example 1 except that the catalyst, CdS, was replaced respectively by Ag carried in an amount of 7 wt.% on a $SiO_2$—ZnO carrier prepared in accordance with the co-precipitation method (weight ratio of $SiO_2$ to $ZnO=1:1$; BET specific surface area=260 m²/g), cadmium sulfate, and $SiO_2$—ZnO—AgO prepared in accordance with the co-precipitation method (weight ratio=1:1:1). Experiment results are shown in Table 1.

TABLE 1

| Ex. No. | Catalyst | Concentration of indole in condensate (%) | Yield of indole (%) |
|---|---|---|---|
| 2 | Ag/$SiO_2$-ZnO | 17.0 | 69 |
| 3 | Cadmium sulfate | 16.6 | 67 |
| 4 | $SiO_2$-ZnO-AgO | 16.1 | 65 |

COMPARATIVE EXAMPLES 1, 2, 3 AND 4

Experiments were carried out in the same manner as in Examples 1, 2, 3 and 4 except that, in each experiment, a 33 wt.% aqueous solution of ethylene glycol was charged at 48 g/hr. together with aniline (75 g/hr) from the feed line 1 without using the feed lines 4 and 5. Experiment results are summarized in Table 2.

TABLE 2

| Comp. Ex. No. | Catalyst | Concentration of indole in condensate (%) | Yield of indole (%) |
|---|---|---|---|
| 1 | Cadmium sulfide | 8.3 | 32 |
| 2 | Ag/$SiO_2$-ZnO | 9.2 | 35 |
| 3 | Cadmium sulfate | 8.1 | 31 |
| 4 | $SiO_2$-ZnO-AgO | 7.9 | 30 |

REFERENTIAL EXAMPLE

A tubular flow reactor having an inner diameter of 10 mm and made of Pyrex (trade mark) glass was packed with 5 ml of cadmium sulfide catalyst and then used for the reaction. The tubular reactor was slowly heated from room temperature to 350° C. and maintained at the latter temperature, as measured on the outer wall of the tubular reactor, while charging hydrogen gas at 20 milliliters/minute into the tubular reactor. The temperature distribution in the catalyst bed was determined. After confirming that the temperature of the catalyst bed was 350° C. uniformly therethroughout, a 33 wt.% aqueous solution of ethylene glycol was charged at 0.48 g/hr. At the same time, aniline was also charged at each of the feeding rates given in Table 3 to the catalyst bed via vaporizers. The reaction effluent was collected for 2 hours after the lapse of a one hour period from the initiation of each reaction, and was subjected to an analysis for determination of the yield of indole. On the other hand, the temperature distribution in the catalyst bed was measured to determine whether any heat spot had been developed. Table 3 shows the relationship between each molar ratio of aniline to ethylene glycol and the yield of indole based on ethylene glycol and temperature of heat spot.

TABLE 3

| Aniline/ ethylene molar ratio | Feed velocity of aniline (g/hr.) | Yield of indole (%) | Temperature of heat spot (°C.) |
|---|---|---|---|
| 3.0 | 0.71 | 33 | 369 |
| 5.0 | 1.19 | 57 | 362 |
| 7.0 | 1.66 | 66 | 359 |
| 10.0 | 2.38 | 69 | 358 |
| 15.0 | 3.56 | 70 | 355 |

What is claimed is:

1. Process for preparing indole in a reactor by reacting aniline and ethylene glycol in a gas phase and in the presence of an effective catalyst, the improvement consisting essentially of feeding ethylene glycol in equal portions under conditions which satisfy the following equation:

$$n \geq (M-1)/(A-1)$$

wherein n is the number of divided supply ports, M is the minimum mole number of aniline per mole of ethylene glycol in the catalyst bed, and A is the mole number of aniline per mole of total ethylene glycol fed in portions into the reactor.

2. The process as claimed in claim 1 wherein the molar ratio of aniline to total ethylene glycol, both charged into a reactor, is in the range of 1 to 5.

3. The process as claimed in claim 1 wherein said catalyst is a catalyst containing the oxide or hydroxide of at least one element selected from the group consisting of Si, Al, B, Sb, Bi, Sn, Pb, Ga, Ti, Zr, Be, Mg, Y, Cu, Ag, Zn, Cd and at least one of the Lanthanide elements.

4. The process as claimed in claim 1 wherein said catalyst is a catalyst containing the sulfide or selenide of at least one element selected from the group consisting of Pd, Pt, Cr, Fe, Ni, Co, Zn, Mo, Cd and W.

5. The process as claimed in claim 1 wherein said catalyst is a catalyst containing an inorganic salt which is, a halide carbonate, nitrate, sulfate, phosphate, pyrophosphate, phosphorus molybdate or silicotungstate of at least one element selected from the group consisting of Fe, Tl, Ca, Mn, Bi, Sr, Y, Al, Zn, Cd, Ni, Mg, In, Be, Co, G, and at least one of the Lanthanide elements.

6. The process as claimed in claim 1 wherein said catalyst is a metallic catalyst containing at least one element selected from the group consisting of Cu, Ag, Pt, Pd, Ni, Co, Fe, Ir, Os, Ra and Rh.

* * * * *